(12) United States Patent
Luan et al.

(10) Patent No.: US 8,039,231 B2
(45) Date of Patent: Oct. 18, 2011

(54) METHODS FOR ENHANCED PRODUCTION OF BONE MORPHOGENETIC PROTEINS

(75) Inventors: Yen-Tung Luan, Chelmsford, MA (US); Wenge Wang, North Chelmsford, MA (US); Gregg Nyberg, Westminster, CO (US); Jose Manuel Gomes, Chelmsford, MA (US); Denis Drapeau, Salem, NH (US); Terry Cardoza, Methuen, MA (US)

(73) Assignee: Wyeth LLC, Madison, NJ (US)

( * ) Notice: Subject to any disclaimer, the term of this patent is extended or adjusted under 35 U.S.C. 154(b) by 16 days.

(21) Appl. No.: 12/425,056

(22) Filed: Apr. 16, 2009

(65) Prior Publication Data

US 2009/0317867 A1  Dec. 24, 2009

Related U.S. Application Data

(60) Provisional application No. 61/045,643, filed on Apr. 17, 2008.

(51) Int. Cl.
*C12P 21/06* (2006.01)
(52) U.S. Cl. ..................................... 435/69.1
(58) Field of Classification Search .................. 435/69.1
See application file for complete search history.

(56) References Cited

U.S. PATENT DOCUMENTS

| | | |
|---|---|---|
| 5,013,649 A | 5/1991 | Wang et al. |
| 5,318,898 A | 6/1994 | Israel |
| 5,516,654 A | 5/1996 | Israel |
| 5,830,761 A | 11/1998 | Drapeau et al. |
| 7,294,484 B2 | 11/2007 | Drapeau et al. |
| 7,429,491 B2 | 9/2008 | Luan et al. |
| 2003/0087372 A1 | 5/2003 | DelaCruz et al. |
| 2005/0070013 A1 | 3/2005 | Luan et al. |

FOREIGN PATENT DOCUMENTS

| | | |
|---|---|---|
| WO | WO92/17584 | 10/1992 |
| WO | WO 99/31120 | 6/1999 |
| WO | WO02/077006 | 10/2002 |
| WO | WO2006/026447 | 3/2006 |

OTHER PUBLICATIONS

Drapeau et al., "Extracellular insulin degrading activity creates instability in a CHO-based batch-refeed continuous process", *Cytotechnology* 15: 103-09 (1994).

Long et al., "Expression, purification, and renaturation of bone Morphogenetic protein-2 from *Escherichia coli*", Protein Expression and Purification Academic Press, San Diego, CA, vol. 46, No. 2, pp. 374-378, Apr. 1, 2006.

Wang et al., "Recombinant Human Bone Morphogenetic Protein Induces Bone Formation", Proceedings of the National Academy of Sciences of USA, National Academy of Science, Washington, D.C., vol. 87, No. 6, pp. 2220-2224, Mar. 1, 1990.

PCT International Search Report & Written Opinion, PCT/US2009/040789, Aug. 10, 2009.

*Primary Examiner* — Maryam Monshipouri

(57) ABSTRACT

Methods and processes for improved recombinant protein production are provided. The methods are useful for production of growth factors, particularly those of the TGF-β superfamily, including bone morphogenetic proteins (BMPs), such as BMP-2. Suitable host cells are cultured in media where iron is present at a concentration of at least 2.25 μM and if pyridoxal is present, it makes up less than 55% of the molar concentration of vitamin B6 in the media.

47 Claims, 7 Drawing Sheets

METHODS FOR ENHANCED PRODUCTION OF BONE MORPHOGENETIC PROTEINS

This application claims the benefit of the earlier filing date of U.S. provisional application No. 61/045,643, filed Apr. 17, 2008, which is incorporated by reference herein in its entirety.

The present invention relates to the field of recombinant protein production. In particular, the invention is directed to methods of producing peptide growth factors, including bone morphogenetic proteins (BMPs).

Members of the transforming growth factor-beta (TGF-β) superfamily possess physiologically important growth-regulatory and morphogenetic properties (Kingsley et al., *Genes Dev.* 8:133-146 (1994); Hoodless et al., *Curr. Topics Microbiol. Immunol* 228:235-272 (1998)). Bone morphogenetic proteins (BMPs) are members of the TGF-β superfamily of growth and differentiation factors (Rosen et al., *Principles of Bone Biology* 2:919-928 (2002)). Some of the first evidence that BMPs existed was demineralized bone's ability to induce new bone when implanted into muscle (Urist et al., *Science* 150:893-99 (1965)). BMPs were subsequently biochemically purified from demineralized bone (Wang et al., *PNAS* 85: 9484-9488 (1988)) and cloned by hybridization of radiolabeled oligonucleotides designed from peptide fragments of the purified proteins (Wozney et al., *Science* 242:1528-1534 (1988)). Cloned BMPs have been recombinantly expressed and retain their function. BMPs are typically produced recombinantly, due to the difficulty, lack of purity, and low yield, associated with biochemical purification from natural sources such as, e.g., bone.

BMP-2 and related proteins BMP-4, BMP-5, BMP-6, BMP-7 (also known as OP-1), BMP-8 (also known as OP-2), BMP-9, and BMP-10 are known to mediate the growth and repair of bone and cartilage tissue. BMP-2 is currently in clinical use for treating open and non-union fractures, spinal fusions (as part of the INFUSE™ medical device), and for orthodontic indications. The availability and cost of this important therapeutic are governed, in part, by the titer of the mammalian cell cultures used in its production. However, culture conditions that produce suitable cell titers on a "laboratory scale" may not scale-up to the large manufacturing scale necessary to meet the rising demand for these proteins. Accordingly, a need exists for methods of producing recombinant proteins, such as BMP-2, by increasing cell titers during production and where the methods are suitable for use on a manufacturing scale.

The present invention provides methods of producing recombinant proteins on a manufacturing scale by supporting high host cell titers, resulting in an increase in protein yield. The invention is based, in part, on the discovery that a defined culture media supplemented with trace metals support higher harvest cell titers of CHO cells cultured in a bioreactor system by a batch-refeed process on a manufacturing scale. Without the supplement of metals, the same media supported growth on a small (laboratory-scale) bioreactor but failed to "scale-up" to a manufacture-scale bioreactor. Titer consistency was further improved when the pyridoxal in the medium was replaced with pyridoxine.

Thus, in one aspect, the invention provides a method of recombinant protein expression comprising the steps of culturing a suitable host cell comprising a nucleic acid encoding a protein of interest in a defined culture medium where iron is present at a concentration of at least about 2.25 µM and if pyridoxal is present, it makes up less than about 55% of the molar concentration of vitamin B6 in the media and recovering the protein of interest. In some embodiments, the iron is present at a concentration of at least about 5 µM. The media may further comprise copper at a concentration of at least about 10 nM and zinc at a concentration of at least about 2 µM. In some embodiments, if pyrodoxal is present in the medium, it is present at a concentration of less than about 15 µM. In particular embodiments, if pyrodoxal is present, it is present at a concentration of less than about 15 µM and makes up less than about 55% of the molar concentration of vitamin B6 in the media. In some embodiments, if pyrodoxal is present in the medium, it is either present at a concentration of less than about 15 µM or makes up less than about 55% of the molar concentration of vitamin B6 in the media.

In some embodiments, the host cell is mammalian cell, e.g., a CHO cell. In certain embodiments, the protein of interest is a member of the TGF-β superfamily, e.g., a BMP, e.g., a BMP-2.

In certain embodiments, the medium contains vitamin B6 at a total concentration of at least about 15 µM. In some embodiments, pyridoxal, if present in the culture medium, makes up no more than about 55% of the total molar concentration of vitamin B6 in the medium. In more particular embodiments, the vitamin B6 has a ratio of pyridoxal to pyridoxine of less than about 1.2. In still more particular embodiments, the medium contains no pyridoxal.

In a particular embodiment, the invention provides a method of BMP-2 production which includes the steps of culturing a suitable host cell comprising a DNA molecule encoding a BMP-2 protein in a culture medium comprising iron at a concentration of at least about 2.5 µM and vitamin B6 at a concentration of at least about 15 µM, and where if pyridoxal is present, it makes up less than about 55% of the molar concentration of vitamin B6 in the media and then recovering a BMP-2 protein.

In some embodiments, the media can also contain amino acids at a total concentration of at least about 20 mM. The medium may contain L-cystine at a concentration of at least about 0.5 mM. In particular embodiments, the medium also contains L-glutamic acid at a concentration of no more than about 0.3 mM.

In certain embodiments, the medium may also contain a polyanionic compound, e.g., dextran sulfate, at a concentration of at least about 10 mg/L. In some embodiments, the medium may have an initial osmolarity of between about 260 and 380 mOsm.

In certain embodiments, the methods of the invention are suitable for culturing cells grown in a batch refeed process. In particular embodiments, the cells are grown in a stirred tank bioreactor with a capacity of at least about 3 L. In still more particular embodiments, the culture temperature is kept essentially constant. In some embodiments, the methods of the invention use culture media that support a harvest cell density of at least about $4.0 \times 10^6$ cells/mL.

Accordingly, in one aspect, the invention provides a process or method for BMP-2 production, which includes the steps of culturing a CHO cell containing a DNA molecule encoding a BMP-2 protein in a culture medium comprising iron at a concentration of at least about 2.5 µM, amino acids at a total concentration of at least about 20 mM, L-cystine at a concentration of at least 0.5 mM, dextran sulfate at a concentration of at least about 10 mg/L, and vitamin B6 at a concentration of at least about 15 µM and where if pyridoxal is present, it makes up less than about 55% of the molar concentration of vitamin B6 in the media; and then recovering a BMP-2 protein. In particular embodiments, the media may further comprise copper at a concentration of at least about 10 nM. In still more particular embodiments, the media may further comprise zinc at a concentration of at least about 0.2 µM.

In some embodiments, the invention provides a method of producing BMP-2 which includes the step of culturing a suitable host cell comprising a DNA molecule encoding a BMP-2 protein in a culture medium comprising iron at a concentration of at least about 2.5 µM and vitamin B6 at a concentration of at least about 15 µM, and where if pyridoxal is present, it makes up less than about 55% of the molar concentration of vitamin B6 in the media, and then recovering a BMP-2 protein.

In some embodiments, any of the methods of the invention may further comprise the step of purifying or isolating the protein of interest, e.g., BMP-2. In some embodiments, the purified or isolated protein can be formulated, e.g, as a pharmaceutical. In particular embodiments, the purification comprises one or more column chromatography purifications, e.g., a butyl sepharose column purification.

In another aspect, the invention provides a product produced by any of the methods of the invention. In some embodiments, the product may be used to treat, or used to prepare a medicament to treat a patient, e.g., a mammal, e.g., a human, having a defect, injury, disease, or disorder of bone tissue by, for example, promoting bone growth, generation, healing, or repair.

In another aspect, the invention provides cell culture medium substantially as described herein. In particular embodiments the cell culture medium is substantially similar to those described in Tables 3 and 4.

EXEMPLARY EMBODIMENTS

Figure 1:
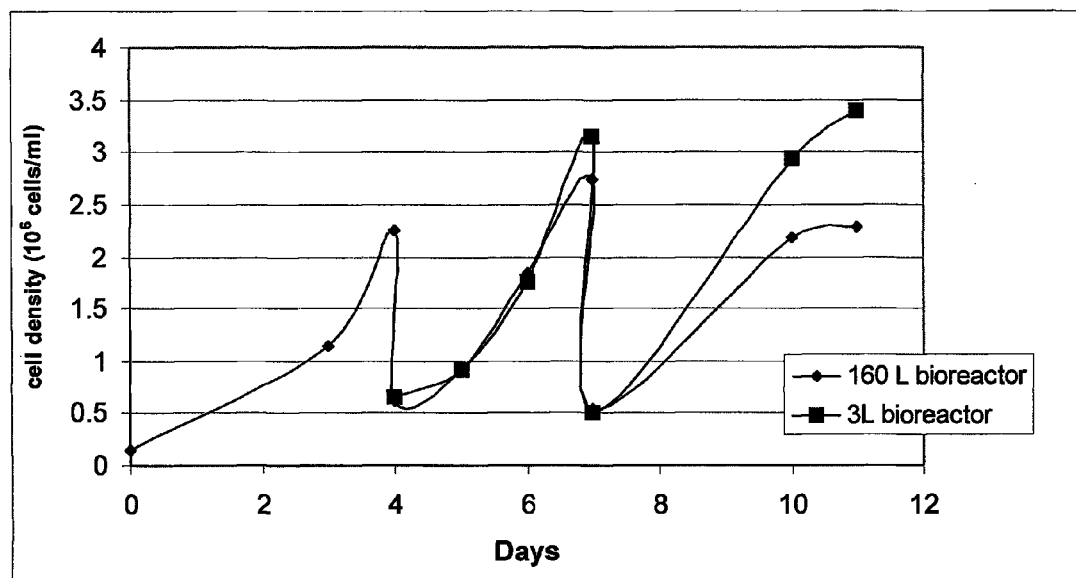
FIG. 1 is a plot of cell density over time in a batch refeed process in 3 L and 160 L bioreactors.

It was discovered that consistent, high-density cultures can be achieved on a manufacturing scale by culturing a BMP-2 expressing cells in media supplemented with iron, copper, and zinc, also containing dextran sulfate, wherein vitamin B6 is present in the media at a concentration of at least 15 µM, and the ratio of pyridoxal to pyridoxine in the vitamin B6 is less than 1.2.

Media

Culture medium suitable for use in the methods of the invention will typically contain nutrients needed to support the growth of the cultured cells, including vitamins, minerals, fatty acids, amino acids, a carbon source (e.g. dextrose), and optionally growth factors, including, e.g., insulin and transferrin, or antibiotics. In some embodiments, the culture medium comprises a basal medium, such as, e.g., Dulbecco's Modified Eagle's Medium (DMEM), Ham's F-12, a Roswell Park Memorial Institute (RPMI) medium, or combinations thereof.

In certain embodiments, the culture medium is a chemically defined medium, i.e., it is serum free. It is to be understood that in this application, unless indicated otherwise, a concentration of a component in the medium is a starting concentration, i.e., the concentration of that component in fresh medium, before being applied to the cultured cells. As is known in the art, concentrations of particular components will change as the cells undergo metabolic processes or through spontaneous chemical reactions.

In some embodiments, the culture medium comprises iron at a concentration of at least about 2.25, 5, 5.5, 8, 10, 12, 14, 15, 20, 25, 30 µM, or more. In more particular embodiments, the iron is present at a concentration of about 5 µM. In still more particular embodiments, the iron is present at a concentration of about 5.5 µM. In some embodiments, iron is present at a concentration of between about 5.5 and 15 µM. It should be understood that for all numerical bounds describing some parameter in this application, e.g., "at least," "less than," or "more than," the description also necessarily describes any range bounded by the recited values.

The culture medium may contain other metals including copper and zinc. Copper may be present at a concentration of at least about 5, 10, 12, 15, 30, 50, 75, 100, 150, 200, 250 nM, or more. In particular embodiments, the copper is present at a concentration of at least about 10 nM. In still more particular embodiments, the copper is present at a concentration of about 74 µM. The culture medium may also contain zinc at a concentration of at least about 0.1, 0.2, 0.5, 1.0, 2.0, 3.0, 4.0, 4.2, 4.5, 4.8, 5.0 µM, or more. In particular embodiments, zinc is present at a concentration of about 4.2 µM. In some embodiments, the culture medium contains iron and copper as described above, e.g., iron is present at a concentration of at least about 2.25, 5, 5.5, 8, 10, 12, 14,15, 20, 25, 30 µM and copper at a concentration of at least about 5, 10, 12, 15, 30, 50, 75, 100, 150, 200, 250 nM. In certain embodiments, the culture medium contains iron, copper, and zinc as described above. Accordingly, in some embodiments, the culture medium comprises iron at a concentration of between about 2.5 µM and 15 µM, copper at a concentration of between about 10 nM and 150 nM, and zinc at a concentration of between about 2.1 µM and 8.4 µM. In more particular embodiments, the culture medium comprises iron at a concentration of at least about 5 µM, copper at a concentration of at least about 10 nM, and zinc at a concentration of at least about 2 µM.

The culture media for use in the methods of the invention support consistent high harvest cell density during, e.g., batch refeed culture. In some embodiments, culture media for use in the method of the invention support a harvest density of at least about $1.0 \times 10^6$, $1.5 \times 10^6$, $2.0 \times 10^6$, $2.5 \times 10^6$, $3.0 \times 10^6$, $3.5 \times 10^6$, $4.0 \times 10^6$, $4.1 \times 10^6$, $4.2 \times 10^6$, $4.3 \times 10^6$, $4.5 \times 10^6$, $4.8 \times 10^6$, $5.0 \times 10^6$, $5.5 \times 10^6$, $6.0 \times 10^6$, $6.5 \times 10^6$, $7.0 \times 10^6$, $7.5 \times 10^6$, $8.0 \times 10^6$, $8.5 \times 10^6$, $9.0 \times 10^6$, $9.5 \times 10^6$ cells/mL, or more. In more particular embodiments, the culture media support a harvest density of about $4.0 \times 10^6$ to $7.0 \times 10^6$ cells/mL. In certain embodiments, to achieve these harvest densities, the cells are seeded at a density of less than about $0.037 \times 10^6$, $0.075 \times 10^6$, $0.15 \times 10^6$, $0.3 \times 10^6$, $0.6 \times 10^6$, $1.2 \times 10^6$, or $2.4 \times 10^6$ cells/mL, or more. In particular embodiments, the cells are seeded at a density of about $0.6 \times 10^6$ cells/mL.

In some embodiments, the culture medium includes vitamin B6, which is known to occur in several forms suitable for use in cell culture, including pyridoxine, pyridoxal, pyridoxamine, pyridoxine 5'-phosphate, pyridoxal 5'-phosphate, pyridoxamine 5'-phosphate, and combinations thereof. In some embodiments, the culture medium contains at least one vitamin B6 selected from pyridoxine, pyridoxamine, pyridoxine 5'-phosphate, pyridoxamine 5'-phosphate, and combinations thereof. In some embodiments, vitamin B6 is present in the culture medium at a total concentration of at least about 5, 10, 15, 20, 25, 30, 35, 40, 45, 50 µM, or more. In particular embodiments, vitamin B6 is present at a concentration of at least about 10 µM. In still more particular embodiments, vitamin B6 is present at a concentration of about 30 µM. In certain embodiments, pyridoxal, if present, makes up no more than about 55, 50, 40, 30, 20, 10, 5, 1, 0.1% of the molar concentration of vitamin B6 in the culture medium. In some embodiments, if present in the culture medium, pyridoxal is present at a concentration of less than about 20, 15, 10, 8, 6, 5, 4, 3, 2, 1 µM. In some embodiments the culture medium has a ratio of pyridoxal to pyridoxine of between 0 and 1.2. In more particular embodiments, the ratio of pyridoxal to pyridoxine in the culture medium is less than 1.2, e.g., less than about 1.1, 1.0, 0.9, 0.7, 0.5, 0.4, 0.3, or 0.1. In still more particular embodiments, the medium contains essentially no pyridoxal.

The culture media for use in the methods of invention will typically provide amino acids to support the growth of the cultured cells and production of the protein of interest. In some embodiments, amino acids may be present in the culture medium in defined proportions, for example, as described in Tables 3 or 4. As is known in the art, hydrolysates of protein preparations (e.g., peptone, bactopeptone, tryptone, casein hydrolysate, or soytone soy hydrolysate) can be used as sources of amino acids. In some embodiments, medium containing defined proportions of amino acids can be supplemented with undefined protein hydrolysates. Alternatively, in some embodiments, undefined hydrolysates serve as the primary source of amino acids. In particular embodiments where hydrolysates are the primary source of amino acids, the medium can be supplemented with one or more particular amino acids as necessary. In some embodiments, the culture medium has a total amino acid concentration of at least about 15, 20, 25, 30, 35, 40 mM, or more. In particular embodiments, the total amino acid content of the medium is at least about 20 mM. In still more particular embodiments, the total amino acid concentration is about 30 mM.

Amino acid proportions and individual amino acid concentrations may be adjusted to accommodate the metabolic needs of the host cell depending on, for example, the cells' growth rate, the cell's metabolic profile, the proportions of the amino acids in the recombinant protein being produced, or to improve the quality of the recombinant protein produced. For example, the portions of rhBMP-2 produced in CHO cells that are in a dissociable dimer with cysteinylated or free sulfhydryl dimers are affected by the concentrations of L-cystine and L-glutamic acid in the medium, as disclosed in, for example, U.S. Pat. No. 5,830,761. Accordingly, in some embodiments, the culture medium comprises L-cystine at a concentration of at least about 0.2, 0.3, 0.4, 0.5, 0.6, 0.7, 0.8, 0.9, 1.0, 1.05, 1.1, 1.2, 1.3, 1.4, 1.5, 2.0, 2.5, 3.0, 3.5, 4.0 mM or more. For example, in particular embodiments, the medium comprises L-cystine at a concentration of about 0.2-4.0 mM. In more particular embodiments, the medium comprises L-cystine at a concentration of about 0.5-4.0 mM. In still more particular embodiments, the medium comprises L-cystine at a concentration of about 0.7-3.0 mM. In some embodiments, L-glutamic acid is present in the culture medium at a concentration of at least about 0.023, 0.05, 0.1, 0.2, 0.3, 0.4, 0.5, 1.0, 1.5, 2.0, 2.5, 3.0, 3.5, 4.0 mM, or more. In particular embodiments the culture medium comprises L-cystine at a concentration of at least about 0.2, 0.3, 0.4, 0.5, 0.6, 0.7, 0.8, 0.9, 1.0, 1.05, 1.1, 1.2, 1.3, 1.4, 1.5, 2.0, 2.5, 3.0, 3.5, 4.0 mM or more and L-glutamic acid at a concentration of at most about 0.023, 0.05, 0.1, 0.2, 0.3, 0.4, 0.5, 1.0, 1.5, 2.0, 2.5, 3.0 mM. In more particular embodiments, L-cystine is present in the culture medium at a concentration of at least about 0.5 mM and L-glutamic acid is present in the culture medium at a concentration of at most about 0.3 mM. In still more particular embodiments, L-cystine is present in the culture medium at a concentration of about 0.7-3.0 mM and L-glutamic acid is present in the culture medium at a concentration of at most about 0.2 mM.

The culture medium may further comprise a polyanionic agent. It is theorized, but not relied upon, that polyanionic agents compete with moieties on the cell surface of cells for binding heparin-molecule-like binding domains on secreted recombinant proteins, e.g., the N-terminus of a mature (proteolytically cleaved) hBMP-2 monomer or dimer. When a secreted protein is bound to a cell's surface, the yield of the protein in solution is reduced. By competing with these elements on a cell's surface, polyanionic agents increase the concentration of the free (not cell-associated) protein in the culture medium. Examples of polyanionic agents include heparin, heparin sulfate, pentosan sulfate, dextran, dextran sulfate, hyaluronic acid, chondroitin, chondroitin sulfate, dermatan sulfate, keratan sulfate, hexuronal-hexosaminoglycan sulfate, inositol hexasulfate, and sucrose octasulfate. In certain embodiments, the polyanionic agent is capable of binding the N-terminus of a mature hBMP-2 monomer with micromolar or nanomolar affinity. In some embodiments, the polyanionic agent is a sulfonated natural polymer, e.g., glycosaminoglycan (GAG) or derivative thereof, where the polymer is at least about 1%, 5%, 10%, 12%, 15%, 18%, 20%, 25%, 30%, 50%, or more, sulfonated. In some embodiments the polyanionic agent is present at a concentration of at least about 1, 5, 10, 20, 50, 75, 100, 200, 400, 600, 800, 1,000 mg/L, or more.

In particular embodiments, the polyanionic agent is dextran sulfate. In more particular embodiments, the dextran sulfate has a molecular weight of between about 5,000 and 500,000 g/mole. In still more particular embodiments, the dextran sulfate has a molecular weight of about 7,000 g/mole. In some embodiments, dextran sulfate is present at a concentration of at least about 10 mg/L. In more particular embodiments, the dextran sulfate is present at a concentration of about 400 mg/L. The use of dextran sulfate in culture medium for producing rhBMP-2 is further described in U.S. Pat. Nos. 5,318,898 and 5,516,654.

The culture medium can be manipulated to maintain certain parameters of the media, e.g., pH, dissolved $O_2$, or osmolarity. In some embodiments, the culture medium is maintained in a particular osmolarity range. In other embodiments, the culture medium is adjusted to a particular starting osmolarity. In particular embodiments, the culture's starting osmolarity is between about 260-380 mOsm. In more particular embodiments the starting osmolarity is between about 280 and 360 mOsm.

In certain embodiments, the culture medium comprises iron at a concentration of at least about 2.5 µM, copper at a concentration of at least about 10 nM, amino acids at a total concentration of at least about 20 mM, dextran sulfate at a concentration of at least about 10 mg/L, and vitamin B6 at a concentration of at least about 15 µM, where the vitamin B6 has a ratio of pyridoxal to pyridoxine of less than about 1.2. In more particular embodiments, the culture medium further comprises zinc at a concentration of at least about 0.2 µM. In very particular embodiments, culture media for use in the invention are described in Table 3 and Table 4, i.e., medium A1, A2, B1, or B2. In still more particular embodiments, the medium is B2. In certain embodiments the medium is substantially similar to B2. By "substantially similar", it is meant that no component of the medium is present at a concentration more than about 0.1, 0.2, 0.5, 1.0,1.5, 2.0, 2.5, or 3.0-fold different (i.e., increase or decrease) than that of medium B2 in Table 4.

In some embodiments, use of an un-defined component may be acceptable and the medium may be supplemented with up to about 0.1, 0.5, 1, 5, 10%, or more fetal bovine serum (FBS). However, even though serum is widely used for mammalian cell culture, there are several problems associated with its use, as discussed in Freshney *Culture of Animal Cells*, John Wiley & Sons, New York, 91-99 (1994). For example, serum contains many unidentified components and therefore is not chemically defined. Indeed, the composition of serum varies from lot to lot, making standardization difficult. Additionally, serum can contain growth inhibitory factors, resulting in suboptimal growth. Finally, serum can contain viruses or other pathogens, making both production and regulatory approval more difficult. Accordingly, serum free media are preferred for use in the methods of the invention.

Proteins

The methods provided by the invention can be used to produce a variety of proteins. In certain embodiments, the protein is a growth factor. In particular embodiments the growth factor is a member of the TGF-β superfamily. In more particular embodiments, the TGF-β family member is a bone morphogenetic protein (BMP).

BMPs are a highly homologous family of proteins, and are separated into subgroups based on even higher levels of homology. Some important subgroups include: BMP-2 and BMP-4; BMP-5, BMP-6, and BMP-7; and BMP-12, BMP-13, and MP-52. In particular, BMPs share an identifying pattern of cysteine residues in the carboxy-terminal region of the protein, which are needed for BMP activity. In certain embodiments, the protein made by the methods of the invention is a BMP selected from BMP-2, BMP-4, BMP-5, BMP-6, BMP-7, BMP-8, BMP-9, BMP-10, BMP-11, BMP-12, BMP-13, BMP-14, BMP-15, BMP-16, BMP-17, BMP-18, and MP-52, including combinations and heterodimers thereof. Typically, BMP refers to a disulfide linked dimeric molecule. In certain embodiments, a BMP may be monomeric. In some embodiments, reference to a BMP includes sequences at least about 70%, 80%, 90%, 95%, 96%, 97%, 98%, 99%, 99.9% or more identical at the amino acid level to the sequence of the mature (lacking a prodomain) region of a known BMP and which retains biological activity (e.g., bone, cartilage, or ligament/tendon-like tissue forming activity). In some embodiments, a BMP may comprise 1, 2, 3, 4, 5, 6, 7, 8, 9, 10, 15, 20, 25, or more amino acid substitutions to a known BMP sequence. BMPs are known in the art and have been identified from a variety of species including mammals such as human, cat, chicken, chimp, cow, dog, goat, horse, macaque, mouse, pig, rabbit, rat, and sheep. Descriptions of BMPs, including, for example, protein and nucleic acid sequences and methods of production, can be found in the following publications: BMP-2, BMP-3, BMP-4, BMP-5, BMP-6, and BMP-7 (disclosed, for example, in U.S. Pat. Nos. 5,013,649; 5,116,738; 5,106,748; 5,187,076; and 5,141,905), BMP-8 (disclosed in PCT WO 91/18098), BMP-9 (disclosed in PCT WO 93/00432), BMP-10 (disclosed in PCT WO 94/26893) BMP-11 (disclosed in PCT WO 94/26892), BMP-12 and BMP-13 (disclosed in PCT WO 95/16035), BMP-15 (disclosed in U.S. Pat. No. 5,635,372), BMP-16 (disclosed in U.S. Pat. No. 6,331,612), MP-52 (disclosed in PCT WO 93/16099), and BMP-17 and BMP-18 (disclosed in U.S. Pat. No. 6,027,917). A reference to these proteins, should be understood to include variants, allelic variants, fragments of, and mutant BMPs, including but not limited to deletion mutants, insertion mutants, and substitution mutants. In particular, reference to any particular BMP should be understood to include N-terminal truncation fragments where at least 1, 3, 5, 7, 9, 10, 11, 12, 13,15, 18, 20, 22, 25, 30, 35, or more residues have been removed from the N terminus of the mature protein.

In particular embodiments of the invention, the BMP is a BMP-2. In some embodiments, the BMP-2 is human BMP-2 (hBMP-2). In still more particular embodiments, the hBMP-2 is mature hBMP-2 ( i.e., Q283-R396 of NCBI accession number NP_001191) and possesses bone and/or cartilage forming activity. In particular embodiments, the hBMP-2 is at least about 88, 89, 90, 92, 94, 95, 96, 98, 99, 99.9% identical at the amino acid level to mature hBMP-2 (Q283-R396 of NCBI accession number NP_001191). Accordingly, in some embodiments, the mature hBMP-2 may contain 1, 2, 3, 4, 5, 6, 7, 8, 9, 10, 11, 12, 13, 14, or 15 amino acid substitutions. In some embodiments, the BMP-2 produced is dimeric. In some embodiments, the BMP-2 produced is monomeric. In certain embodiments, a BMP-2 has an N-terminal truncation of at least 1, 3, 5, 7, 9, 10, 11, 12, 13, or more residues from the N terminus of at least one subunit of the dimeric protein. Assays for BMP-2 activity are known in the art and are disclosed in, e.g., U.S. Pat. No. 5,013,649.

BMP-2 has been identified in numerous species. See, for example, Table 1, which lists the National Center for Biotechnology Information (NCBI) Entrez GeneID for BMP-2 from several species. These GeneIDs may be used to retrieve publicly-available annotated mRNA or protein sequences, for example, at the NCBI world-wide web portal, which may be found at the following uniform resource locator (URL): http://www.ncbi.nlm.nih.gov/sites/entrez?db=gene. As an illustration, the GeneID for human BMP-2 can be used to retrieve the following reference sequences: NM_001200.2 (mRNA) and NP_001191.1 (protein). Similarly for mouse, the BMP-2 reference sequences that can be retrieved include NM_007553.2 (mRNA) and NP_031579.2 (protein). All information associated with GeneIDs referenced in this application, including, for example, genomic loci, genomic sequences, functional annotations, allelic variants, and reference mRNA and protein sequences are hereby incorporated by reference in their entirety. All reference sequences are also incorporated by referenced in their entirety, including annotated features of the sequences, such as exon boundaries of mRNAs or structural features of proteins, e.g., defining the mature region of the proteins.

TABLE 1

| Species | GeneID |
|---|---|
| Human | 650 |
| Mouse | 12156 |
| Chicken | 378779 |
| Rat | 29373 |
| Frog | 548717 |
| Sheep | 443173 |
| Cow | 615037 |
| Pig | 494462 |
| Chimpanzee | 458090 |
| Dog | 477162 |
| Macaque | 718330 |
| Rabbit | 100009349 |

Isolation and Uses

As is known in the art, bone morphogenetic proteins such as BMP-2 are useful as protein-based therapeutics. Accordingly, the methods of the invention may further comprise the step of purification or isolation of the protein recovered from the culture. BMP-2 can be purified by a variety of means known in the art. In particular embodiments, the purification comprises one or more column chromatography purifications, e.g., a butyl sepharose resin purification. In more particular embodiments the butyl sepharose column comprises a resin of butylamine coupled to CNBr-activated sepharose, e.g., sepharose 4B. In some embodiments, the purification may further comprise a column purification step on a heparin-like resin, e.g., a CELLUFINE™ sulfate resin. For example, conditioned medium from the cultured cells, which contains the BMP-2 may be applied to a heparin-like resin containing column, an eluate containing the BMP-2 is obtained from the column, and then is applied to a second column, such as a butyl sepharose column. Additional purification is possible as described in, for example, International Publication No. WO 99/31120, particularly pages 3-7 therein, incorporated by reference.

Once purified, products of the methods of the invention can be further formulated, e.g., as pharmaceuticals. For a general review of pharmaceutical carriers for BMPs, see, for example, Seeherman and Wozney *Cytokine Growth Factor Rev.* 16(3):329-45 (2005) or U.S. Pat. No. 5,385,887. The products of the methods of the invention can be used to treat, or used to prepare a medicament to treat, a defect, injury, disease, or disorder of bone tissue by, for example, promoting bone growth, generation, healing, or repair.

Cells

A wide variety of cells can be used to produce a recombinant protein by the methods provided by the invention. Any cell that can be transformed with recombinant DNA to express a protein of interest, e.g., a BMP, can be used in the methods of the invention. The cells can be from a variety of species, including nematode, worm, insect, amphibian, or mammal, for example, human, primate, ovine, bovine, porcine, equine, feline, canine, or rodent source. In particular embodiments, the cells are from human or rodent. In more particular embodiments, the cells are from hamster.

Cell lines suitable for use in the methods of the invention are well known in the art and widely available. A number of suitable cell lines can be obtained from depositories such as the America Type Culture Collection (ATCC), Manassas, Va. Suitable lines cells invention include a COS cell, a CHO cell, a BHK cell, a Balb/c 3T3 cell, a FRhL-2 cell, a SP2/0 cell, a NSO cell, a TM4 cell, a CV1 cell, a MDCK cell, a BRL cell, a Vero-76 cell, a HeLa cell, a MDCK cell, a HepG2 cell, or a 293 cell. In particular embodiments, the cell is a COS cell, a CHO cell, a BHK cell, a Balb/c 3T3 cell, or a 293 cell. In more particular embodiments, the cell is a CHO cell. The CHO cell may be modified to increase cell titer and/or protein yield. In some embodiments, the CHO cell may have reduced or no expression of the dihydrofolate reductase gene (DHFR; mouse GeneID 13361), e.g., the CHO cell may be heterozygous or homozygous for a hypomorphic (reduced function), null (non-functional), or dominant-negative (null and inhibits functional forms of the enzyme), allele of DHFR and the protein of interest may be cotransfected in a construct containing a functional DHFR gene.

Bioreactor and Conditions

Cells for use in the methods of the invention can be cultured by any means known in the art, e.g., as discussed in Warnock and Al-Rubei *Biotech. Appl. Biochem.* 45:1-12 (2006). Typically, the cells are grown in a bioreactor. Bioreactors can be any size. In some embodiments, the bioreactor is at least about 1 L; 3 L; 20 L; 40 L; 80 L; 100 L; 160 L; 1,900 L; 2,500 L; 12,000 L; 20,000 L; 40,000 L, or more. A bioreactor can support growth of cells in suspension (i.e., anchorage independent growth) or anchored on a substrate. Anchorage-dependent growth can include the use of microcarriers to, e.g., provide a large surface area to volume ratio.

In particular embodiments of the invention, the cells are grown in suspension; i.e., without an anchoring surface. Modalities of anchorage-independent growth are well-known in the art and include growth in, for example, stirred-tank bioreactors and airlift bioreactors. In particular embodiments, the bioreactor is a stirred-tank bioreactor. Cells grown in a particular bioreactor, in turn, can be cultured by a variety of methods known in the art including batch refeed (described further below, see also Drapeau et al., *Cytotechnology* 15(1-3):103-9 (1994)), fed batch (see, e.g., U.S. Pat. Nos. 5,672,502; 6,924,124; or 7,332,303), or perfusion (employing a cell retaining device so waste can be removed from the bioreactor when fresh medium is added, see, e.g., U.S. Pat. Nos. 4,814,278 or 6,607,910) culture methods. In some particular embodiments, the cells are cultured by a batch re-feed process. In more particular embodiments the cells are cultured at an essentially constant temperature. In some embodiments, a suitable culture temperature may be selected from about 31, 32, 33, 34, 35, 36, 37, 38, 39, 40, 41, or 42° C. In some embodiments, the essentially constant temperature may be a narrow range of temperatures, such as 35-39° C. or 36-38° C. In more particular embodiments, the cells are cultured at a constant temperature of about 37° C.

Bioreactors can maintain various physiological parameters of the culture medium including, for example, oxygenation (dissolved $O_2$), pH, osmalarity, temperature, light, and the concentration of particular nutrients (e.g., glucose or amino acids). In certain embodiments, the bioreactor monitors and maintains temperature, pH, and dissolved $O_2$ content. In some embodiments, glucose is fed in batches. For example, cells are grown in a bioreactor by batch refeed. In particular embodiments, a portion of the total culture (i.e., cells and medium) is periodically removed (e.g., harvested) and replaced with fresh medium. In some embodiments, at least about 10, 25, 50, 75, 80, 85, 90, 95, 99%, or more of the total culture is removed periodically and replaced with fresh medium. In more particular embodiments, at least about 75% of the total culture is removed and replaced. In particular embodiments, a portion of the cell culture medium is removed about every 6, 12, 18, 24, 30, 36, 42, or 48 hours, or every 1, 2, 3, 4, 5, 6, 7, 8, 9, 10, or more days. In more particular embodiments, a portion of the culture medium is removed and replaced every 3 days. In other embodiments, a portion of the total culture is removed and replaced about every 1, 2, 3, 4, 5, 6, 7, 8, 9, 10, or more cell division cycles. By "cell division cycle", it is meant the average doubling time of cultured cells during exponential growth—i.e., in rich culture medium, in the absence of, e.g., contact inhibition.

In certain embodiments, cell titer and/or protein yield can be enhanced by limiting or controlling lactate production by the cells. Lactate production can be controlled by limiting the feeding of glucose to the cultured cells in a restricted manner, e.g., as disclosed in U.S. Patent Publication No. 2005/0070013, published Mar. 31, 2005 (see also U.S. Pat. No. 7,429,491).

For all patents, applications, GeneIDs, Reference Sequences, or other reference cited herein, it should be understood that it is incorporated by reference in its entirety for all purposes as well as for the proposition that is recited. Where any conflict exists between a document incorporated by reference and the present application, this application will dominate.

Examples

Example 1

Scale-up Problem During rhBMP-2 Production

During development of a BMP-2 production process, a scale-up problem was observed with high cell density cultures of CHO cells that coexpress rhBMP-2 and dihydrofolate reductase (DHFR) (herein known as EMC-G5 cells) in a 1,900-liter bioreactor. High cell density cultures were inoculated at $0.60 \times 10^6$ cells/mL for a 3-day batch, or $0.30 \times 10^6$ cells/mL for a 4-day batch. During the first passage of the batch-refeed process, the final cell density commonly reached $3.0 \times 10^6$ cells/mL, but the final cell density of the following passages declined progressively. For example, three passages would result in harvest cell densities of $3.0 \times 10^6$, $1.6 \times 10^6$, and $1.0 \times 10^6$ cells/mL, respectively. Such declining growth rates resulted in lower amounts of BMP-2 protein in the culture medium and overall productivity was lower than desired. The declining growth rates were not reproducible at the 3-liter scale. A 160-liter bioreactor was used as a model for investigating this issue. The declining harvest cell density was seen in the 160 L bioreactor, as shown in FIG. 1.

Additional experiments showed the same difficulty. In one trial, the first high density passage reached a final cell density of $2.99 \times 10^6$, while the second passage reached only $2.28 \times 10^6$ cells/mL. The reactor was inoculated again under control conditions with a pre-passage, then the first and second high density passages reached final cell densities of $2.65 \times 10^6$ and $1.49 \times 10^6$ cells/mL, respectively. Both control experiments demonstrated the scale-up problem in which the first high seed passage reaches a high final density but the growth rate of the following passage declines significantly. The BMP-2 titer and specific productivity data showed similar trends.

Figure 2:
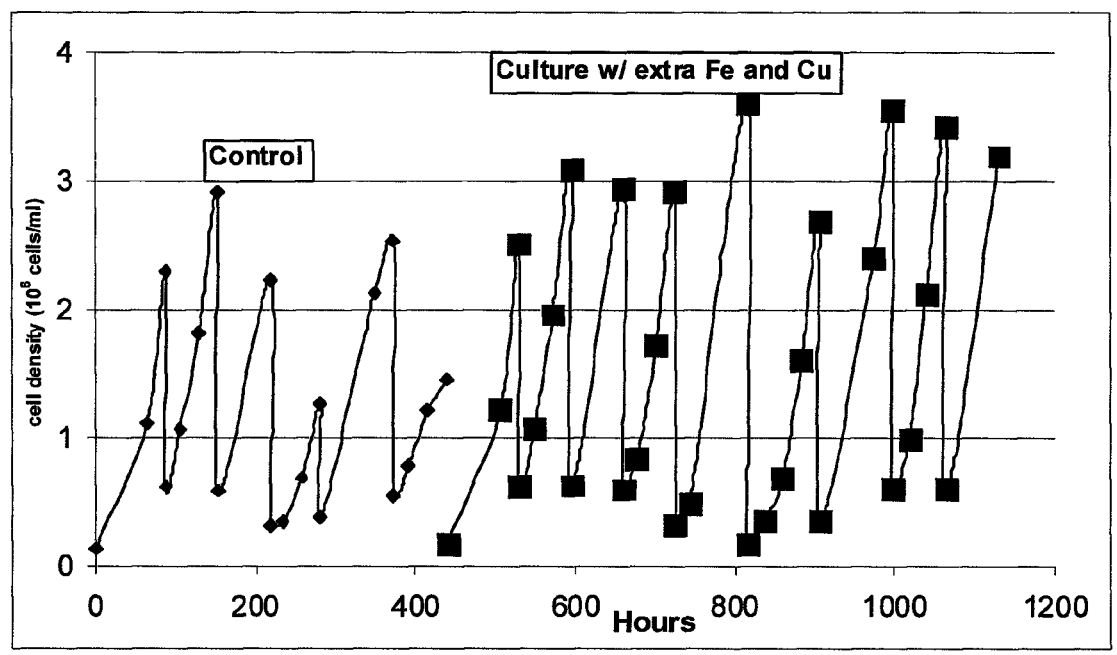
FIG. 2 is a plot of cell density over time in a batch refeed process in a 160 L bioreactor for cells grown in media with and without supplemental iron and copper.

The addition of trace elements D ("trace D") to the growth media eliminated the scale-up problems in the culture medium. Trace D consists of 3 μM iron, 3 μM zinc, and 0.03 μM copper. With Trace D, high-seed batches (3-day and 4-day) consistently reached harvest densities of $3.0 \times 10^6$ cells/mL or higher. The growth rate and specific productivity remained high as well. This indicates that trace D positively affected the cell growth characteristics. The results of an experiment in which cells were grown in media with and without supplemental iron and copper is shown in FIG. 2.

In attempting to discover which component of trace D is most important, media supplemented with copper only was tested (not shown). After the first high seed batch reached over $3.0 \times 10^6$ cells/mL, the following two batches showed declining growth rates, similar to the behavior of the control batches (without trace D). The declining growth rates of the three high-seed passages shows that copper alone was not effective in improving the scale-up problem.

Example 2

Dextran Sulfate Eliminates Chromatogram Abnormality

During these trace metal evaluations, an abnormal shoulder was observed on the second peak of the Size Exclusion chromatogram (CEX) from rhBMP-2 produced in previous high-density cultures. It was found that a low level of dextran sulfate in the media (10 mg/L instead of 200 mg/L) resulted in a much higher percentage of shoulder peak after incubation with phosphate (approximately 12%, versus approximately 4%, respectively). A dextran sulfate dose response experiment showed that higher levels of dextran sulfate in the cell culture media reduced the amount of observed shoulder peak in a dose-dependent manner. Dextran sulfate had previously been shown to increase protein yield during BMP-2 production. See, e.g., U.S. Pat. Nos. 5,318,898 and 5,516,654.

Example 3.1

Declining Cell Titer in Metal-Supplemented Media

Figure 3:
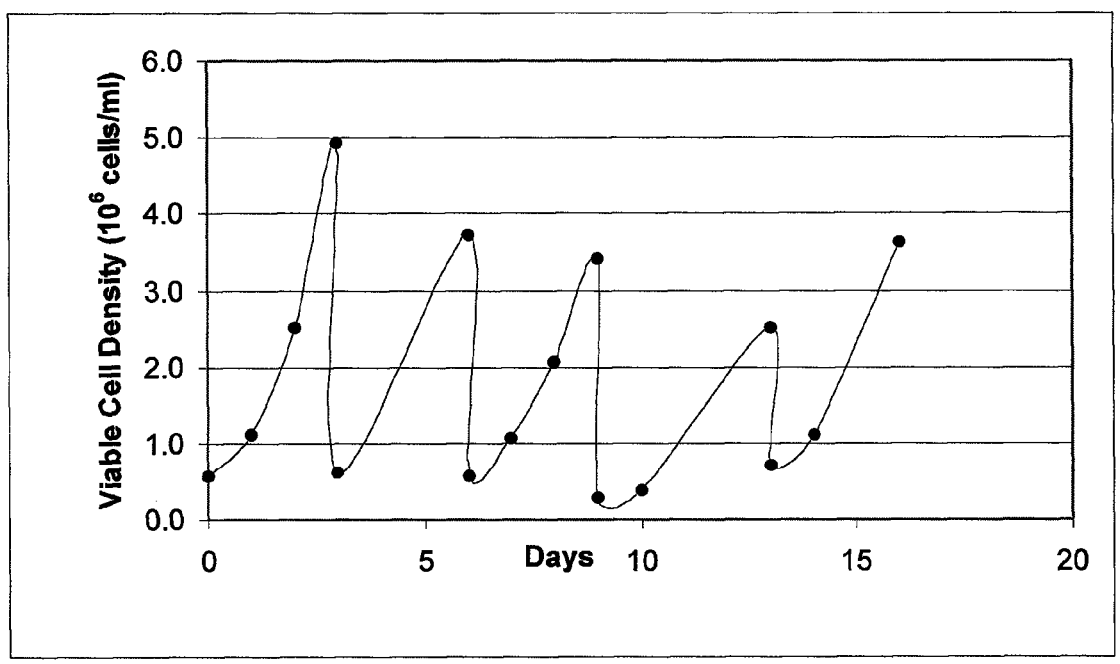
FIG. 3 is a plot of viable cell density over time in a batch refeed process in a 160 L bioreactor for cells grown in media supplemented with iron and copper.

When iron and copper concentrations were enriched in the culture medium, it was occasionally observed that cell growth was not stable, even in lab-scale bioreactors. See FIG. 3. It was hypothesized that the additional metals may interact with other medium component(s) and result in unstable culture growth.

Figure 4:
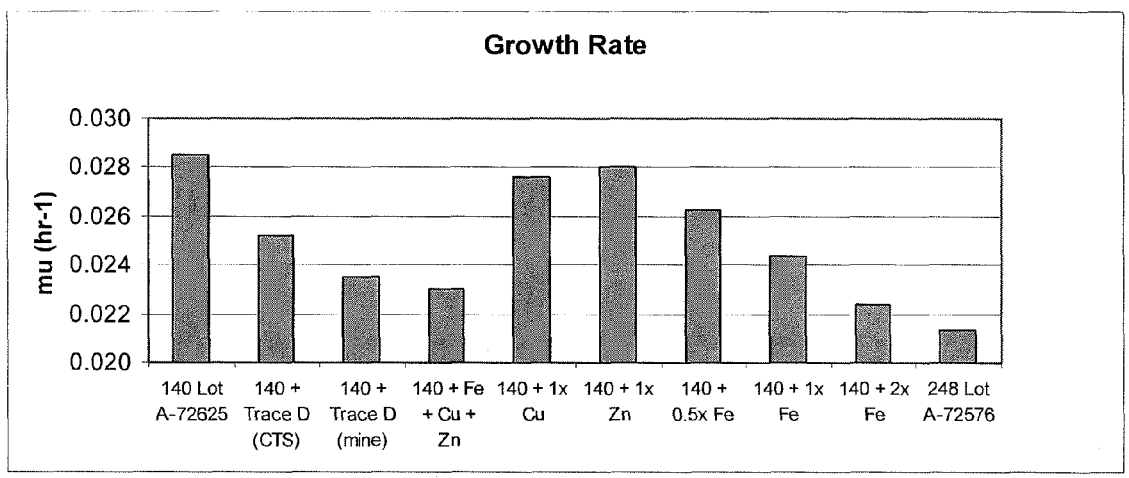
FIG. 4 is a series of bar graphs showing the growth rate of cells grown in flasks with different media and different metal concentrations.

In preliminary experiments in tissue culture flasks (FIG. 4), cells were seeded at a density of $0.08 \times 10^6$ cells/mL and grown for four days. Media A1 (140) supplemented with copper or zinc alone supported growth rates comparable to the unsupplemented media, while trace D-supplementation (additional iron, copper, and zinc) resulted in lower growth rates. The cells also exhibited a dose-dependent decrease in growth rate when media A1 was supplemented with iron alone. Cells grown in media B1 (248) exhibited reduced growth rates similar to cells grown in media A1 supplemented with iron.

Example 3.2

Pyridoxal-Iron Interaction Results in Reduced Growth Rate

In a further study, media A1, which elicited the growth rate defect was compared to media A2, which did not elicit the growth rate defect. It was noted that medium A1 contains principally pyridoxal, while medium A2 contains only pyridoxine. BMP-2 EMC G5 cells were growth in media A1 and media A2 at different iron concentrations and with and without pyridoxal. The iron and vitamin B6 content of media A1 and A2 are summarized in Table 2.

TABLE 2

| Media | Iron (μM) | Pyridoxal (μM) | Pyridoxine (μM) |
|---|---|---|---|
| Media A1, 3 uM Fe | 3 | 10 | 0.15 |
| Media A1, 12 uM Fe | 12 | 10 | 0.15 |
| Media A2, 3 uM Fe | 3 | 0 | 10 |
| Media A2, 12 uM Fe | 12 | 0 | 10 |
| Media A2, 3 uM Fe, 2.5 mg/L Pyridoxal | 3 | 12 | 10 |
| Media A2, 12 uM Fe, 2.5 mg/L Pyridoxal | 12 | 12 | 10 |

Figure 5:
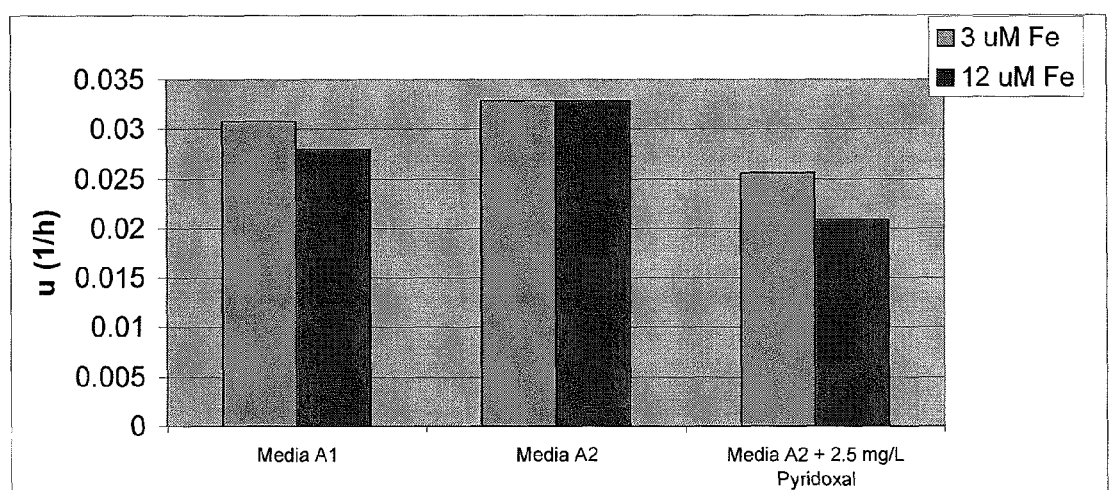
FIG. 5 is a series of bar graphs showing the growth rate of cells grown in culture dishes with different media and different iron concentrations.

Cells were cultured in tissue culture dishes in an incubator maintained at 37° C. with 7% $CO_2$ for 3 days. Cells were seeded at $0.15 \times 10^6$ cells/mL and harvested at the end of 3 days. Day 3 cells were counted on a CASY counter to obtain the final cell density (in units of $10^6$ cells/mL). The growth rate was then calculated by the following equation: Growth rate (u)=ln (final cell density/initial cell density)/culture time (hours). Results are shown in FIG. 5.

It was discovered that pyridoxial, but not pyridoxine, was the component that interacts with iron and caused inconsistent culture performance. Pyridoxine is the precursor of pyridoxal. They are exchangeable as vitamin B6 in culture medium and act as cofactors for transamination, decarboxylation, and deamination. For most cell culture processes, it makes no difference if media contains pyridoxine, pyridoxal, or both. However, pyridoxal at certain concentrations interacts with the increased amount of iron and negatively affects the rhBMP-2 production process. As shown in FIG. 5, medium A1 elicits a growth rate defect relative to medium A2, which can be exacerbated by additional iron. When supplemented with pyridoxal, medium A2 elicits a growth rate defect in an iron dose-dependent manner. Thus, the combination of higher iron concentration and higher concentrations or proportions of pyridoxal in the culture medium results in unstable and sub-optimal culture growth.

Example 4

Robust Increase in Cell Density and Protein Titer

Figure 6:
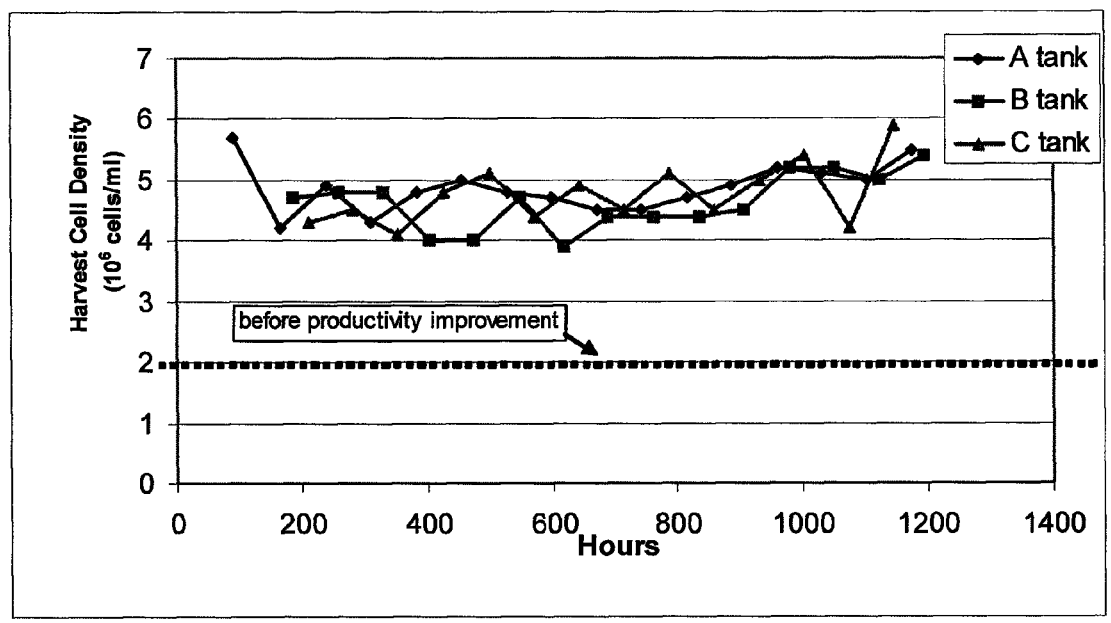
FIG. 6 is a plot of harvest cell density over time in a batch refeed process in 2500 L bioreactors of cells grown according to the methods of the invention. The dashed line indicates average harvest densities of earlier processes.
Figure 7:
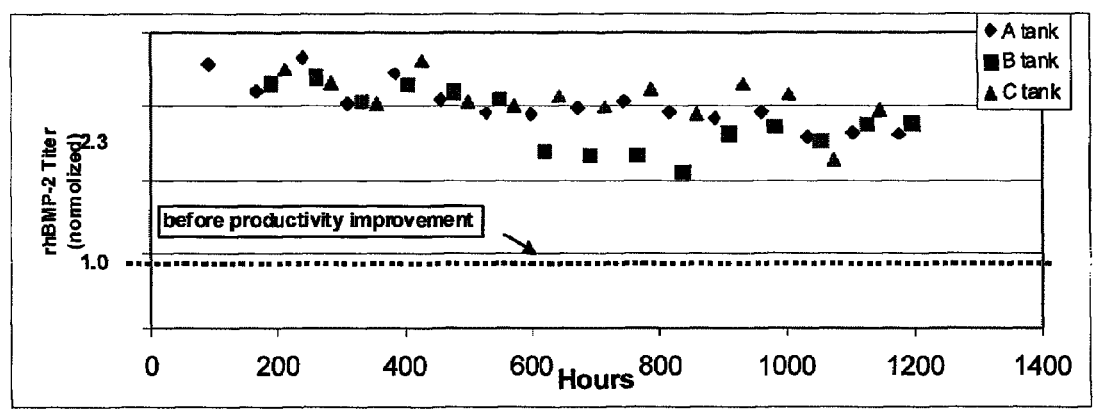
FIG. 7 is a plot of rhBMP-2 harvest titer over time for the cultures described in FIG. 6. The dashed line indicates average rhBMP-2 normalized harvest titer of earlier processes.

After a further medium modification (resulting in medium B2), which eliminated pyridoxal from the medium, cell growth and BMP-2 productivity were consistent, and exhibited a two-fold increase in productivity in small-scale bioreactors as well as in commercial-scale bioreactors relative to earlier processes. See FIG. 6 and FIG. 7. Thus, the modifications to culture medium described in this application eliminate growth defects that occurred during scale-up of recombinant protein production to a commercial-scale, resulting substantial increases in the yield of high-quality recombinant protein.

The cell line used to produce recombinant human bone morphogenetic protein-2 (rhBMP-2) in manufacturing was a Chinese Hamster Ovary (CHO) line that coexpresses BMP-2 and DHFR, referred to herein as EMC-G5. The cells were cultured in 2,500-liter working volume bioreactors inoculated at targeted cell densities of $0.6 \times 10^6$ cells/mL. Cells were cultured in Medium B2 (see Table 4). The temperature of the cultures was maintained at 37° C. The pH of the culture was allowed to decline over the first several hours of a passage down to a set point of 7.10 and was maintained there by the addition of titrant. The initial pH of medium B2 was ~7.30. Cultures were serially passaged at each inoculum cell density for two 3-day passages and two 4-day passages. The pH probes were calibrated on-line according to measurements from a blood-gas analyzer (BGA). Cell densities and viabilities were determined by the manual count using microscope, using the trypan blue exclusion to determine viability. Conditioned medium from all cultures after each passage was harvested by centrifugation and then filtered.

Tables 3 and 4 show the formulations of media used in these studies.

TABLE 3

| Amino Acids | Component | Media A1 mM | Media A2 mM |
|---|---|---|---|
| | Ala | 0.200 | 0.100 |
| | Arginine | 2.520 | 0.550 |
| | Arsparagine | 0.800 | 0.450 |
| | Aspartic acid | 0.200 | 0.250 |
| | Cys HCl, H2O | 0.400 | 0.400 |
| | Cystine 2HCl | 1.400 | 1.400 |
| | Glutamic acid | 0.200 | 0.100 |
| | Glutamine | 8.000 | 8.000 |

TABLE 3-continued

| | | | |
|---|---|---|---|
| | Glycine | 0.400 | 0.100 |
| | His HCl H2O | 0.220 | 0.175 |
| | isoleucine | 0.800 | 0.450 |
| | leucine | 0.800 | 0.650 |
| | Lysine HCl | 0.800 | 0.500 |
| | Methionine | 0.200 | 0.200 |
| | Phenylalanine | 0.400 | 0.250 |
| | proline | 0.600 | 0.300 |
| | serine | 2.000 | 2.000 |
| | threonine | 0.800 | 0.400 |
| | tryptophan | 0.080 | 0.080 |
| | tyrosine 2Na | 0.400 | 0.200 |
| | L-valine | 0.800 | 0.400 |
| Vitamins | | μM | μM |
| | Biotin | 0.830 | 0.850 |
| | D-Calcium pantothenate | 4.700 | 4.700 |
| | choline chloride | 64.600 | 64.500 |
| | folic acid | 6.000 | 6.000 |
| | I-inositol | 70.000 | 70.000 |
| | nicotinamide | 16.500 | 16.500 |
| | pyridoxine HCl | 0.150 | 10.000 |
| | pyridoxal HCl | 10.000 | 0.000 |
| | riboflavin | 0.530 | 0.550 |
| | thiamine HCl | 6.500 | 6.500 |
| | vitamine B12 | 0.500 | 0.500 |
| Other components | | μM | μM |
| | D-Glucose | 7.7 g/L | 7.2 g/L |
| | Sodium pyruvate | 500.000 | 500.000 |
| | linoleic acid | 0.150 | 0.075 |
| | thioctic acid | 0.500 | 0.250 |
| | putrescine 2HCl | 12.900 | 12.900 |
| Inorganic salts | | mM | mM |
| | NaCl | 94.860 | 94.860 |
| | KCl | 4.200 | 4.200 |
| | CaCl2 | 1.050 | 1.050 |
| | Na2HPO4 | 0.500 | 0.500 |
| | NaH2PO4•2H2O | 0.450 | 0.450 |
| | MgCl2 | 0.300 | 0.300 |
| | MgSO4 | 0.400 | 0.400 |
| | | μM | μM |
| | CuSO4•5H2O | 0.005 | 0.002 |
| | FeSO4•7H2O | 2.250 | 2.250 |
| | Fe(NO3)3•9H2O | 0.125 | |
| | ZnSO4•7H2O | 1.500 | 0.400 |
| Other additions | PVA | 2.4 g/L | 2.4 g/L |
| | Insulin | 10 mg/L | 10 mg/L |
| | Hydrocortisone | 72 μg/L | 72 μg/L |
| | NaHCO3 | 2.44 g/L | 2.44 g/L |
| | Dextran Sulfate | 200 mg/L | 200 mg/L |
| | Sodium Selenite | 0.029 μM | 0.029 μM |

TABLE 4

| Amino Acids | Component | Media B1 mM | Media B2 mM |
|---|---|---|---|
| | Ala | 0.28 | 0.30 |
| | Arginine | 2.44 | 2.99 |
| | AsparagineH2O | 1.16 | 1.35 |
| | Aspartic acid | 0.40 | 0.50 |
| | Cys HCl, H2O | 0.40 | 0.40 |
| | Cystine 2HCl | 1.40 | 1.40 |
| | Glutamic acid | 0.28 | 0.20 |
| | Glutamine | 8.00 | 8.00 |
| | glycine | 0.48 | 0.30 |
| | His HCl H2O | 0.36 | 0.53 |
| | isoleucine | 1.16 | 1.35 |

TABLE 4-continued

|  |  |  |  |
|---|---|---:|---:|
|  | leucine | 1.32 | 1.95 |
|  | Lysine HCl | 1.20 | 1.50 |
|  | Methionine | 0.36 | 0.60 |
|  | Phenylalanine | 0.60 | 0.75 |
|  | proline | 0.84 | 0.90 |
|  | serine | 2.60 | 3.35 |
|  | threonine | 1.12 | 1.20 |
|  | tryptophan | 0.14 | 0.24 |
|  | tyrosine 2Na 2H2O | 0.56 | 0.40 |
|  | L-valine | 1.12 | 1.20 |
| Vitamins |  | μM | μM |
|  | Biotin | 1.51 | 2.55 |
|  | D-Calcium pantothenate | 8.46 | 14.10 |
|  | choline chloride | 116.20 | 193.50 |
|  | folic acid | 10.80 | 12.00 |
|  | I-inositol | 126.00 | 210.00 |
|  | nicotinamide | 29.70 | 49.50 |
|  | pyridoxine HCl | 8.15 | 30.00 |
|  | pyridoxal HCl | 10.00 | 0.00 |
|  | riboflavin | 0.97 | 1.65 |
|  | thiamine HCl | 11.70 | 19.50 |
|  | vitamin B12 | 0.90 | 1.50 |
| Other components |  | μM | μM |
|  | D-Glucose | 11.1 g/L | 11.1 g/L |
|  | Sodium pyruvate | 500.00 | 0.00 |
|  | linoleic acid | 0.21 | 0.15 |
|  | thioctic acid | 0.70 | 0.50 |
|  | putrescine 2HCl | 15.40 | 15.00 |
| Inorganic salts |  | mM | mM |
|  | NaCl | 3.7 g/L | 3.6 g/L |
|  | KCl | 4.20 | 4.20 |
|  | CaCl2 | 1.05 | 1.05 |
|  | Na2HPO4• | 0.50 | 0.50 |
|  | NaH2PO4•2H2O | 0.88 | 0.88 |
|  | MgCl2 | 0.30 | 0.30 |
|  | MgSO4 | 0.44 | 0.44 |
|  |  | μM | μM |
|  | CuSO4•5H2O | 36 nM | 74 nM |
|  | FeSO4•7H2O | 5.50 | 5.50 |
|  | Fe(NO3)3•9H2O | 0.13 |  |
|  | ZnSO4•7H2O | 4.80 | 4.20 |
| Other additions | PVA | 2.4 g/L | 2.4 g/L |
|  | Insulin | 14 mg/L | 14 mg/L |
|  | Hydrocortisone | 86.4 μg/L | 86.4 μg/L |
|  | NaHCO3 | 2.44 g/L | 2.44 g/L |
|  | Dextran Sulfate | 200 mg/L | 400 mg/L |
|  | Sodium Selenite | 0.04 μM | 0.0805 μM |
| Trace cpts. |  | μM | μM |
|  | MnSO4 H2O |  | 0.02 |
|  | CrCl3 |  | 0.01 |
|  | (NH4)6Mo7O24 4H2O |  | 0.02 |
|  | KI |  | 0.02 |
|  | Na2SiO3 9H2O |  | 0.1 |
|  | H3BO3 |  | 0.02 |
|  | H3BO3 |  | 0.02 |
|  | NiSO4 6H2O |  | 0.002 |
|  | NH4VO3 |  | 0.002 |
|  | AlCl3 6H2O |  | 0.0004 |
|  | KBr |  | 0.0004 |
|  | NaF |  | 0.0004 |
|  | GeO2 |  | 0.0004 |
|  | LiCl |  | 0.0004 |
|  | RbCl |  | 0.0004 |
|  | SnCl2 2H2O |  | 0.0004 |

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of BMP-2 production comprising the steps of:
   i) culturing a suitable host cell comprising a DNA molecule encoding a BMP-2 in a culture medium comprising iron at a concentration of at least about 2.25 μM, a polyanionic compound, a total amino acid concentration of 15 mM to 40 mM, and if pyridoxal is present, it makes up less than about 50% of the molar concentration of vitamin B6 in the culture medium; and
   ii) recovering the protein of interest wherein the host cell is cultured in a bioreactor having a capacity greater than about 3 L.

2. The method of claim 1, wherein the iron is at a concentration of at least about 5 μM.

3. The method of claim 1, wherein the culture medium can support a harvest density of at least about $2 \times 10^6$ cells/mL.

4. The method of claim 1, where in the culture medium further comprises at least one vitamin B6 selected from the group consisting of pyridoxine, pyridoxamine, pyridoxine 5'-phosphate, pyridoxamine 5'-phosphate.

5. The method of claim 4, wherein the culture medium has a total vitamin B6 concentration of at least about 15 μM.

6. The method of claim 4, wherein the culture medium has a ratio of pyridoxal to pyridoxine of less than 1.2.

7. The method of claim 6, wherein the ratio of pyridoxal to pyridoxine is less than 0.4.

8. The method of claim 1, wherein the culture medium further comprises copper at a concentration of at least about 10 nM.

9. The method of claim 1, wherein the culture medium further comprises zinc at a concentration of at least about 0.2 μM.

10. The method of claim 1, wherein the polyanionic compound is dextran sulfate.

11. The method of claim 10, wherein the dextran sulfate is present at a concentration of at least about 10mg/L.

12. The method of claim 10, wherein the dextran sulfate is present at a concentration of at least about 100 mg/L.

13. The method of claim 11, wherein the dextran sulfate has a molecular weight of between about 5,000 and 500,000 g/mole.

14. The method of claim 13, wherein the dextran sulfate has a molecular weight of about 7,000 g/mole.

15. The method of claim 1, wherein the culture medium comprises L-cystine at a concentration of at least about 0.5 mM.

16. The method of claim 15, wherein the culture medium comprises L-glutamic acid at a concentration of at most about 0.3 mM.

17. The method of claim 1, wherein the culture medium has an initial osmolarity of between about 260 and 360 mOsm.

18. The method of claim 1, wherein the BMP-2 is a recombinant human BMP-2 (rhBMP-2).

19. The method of claim 1, wherein the suitable host cell is selected from the group consisting of a COS cell, a CHO cell, a BHK cell, a Balb/c 3T3 cell, or a 293 cell.

20. The method of claim 19, wherein the suitable host cell is a CHO cell.

21. The method of claim 20, wherein the CHO cell has a reduced expression of the DHFR gene.

22. The method of claim 1, wherein the suitable host cell is cultured in a bioreactor that has a capacity of at least about 160 L.

23. The method of claim 22, wherein the bioreactor has a capacity of at least about 500 L.

24. The method of claim 23, wherein the bioreactor has a capacity of at least about 2,500 L.

25. The method of claim 24, wherein the bioreactor has a capacity of at least about 12,000 L.

26. The method of claim 23, wherein the host cell is cultured by batch refeed, fed batch, or perfusion.

27. The method of claim 26, where the host cell is cultured by batch refeed.

28. The method of claim 27, where the host cell is cultured at an essentially constant temperature.

29. The method of claim 28, where the temperature is about 36-38° C.

30. The method of claim 1, further comprising the step of purifying the BMP-2 on a butyl sepharose resin.

31. The method of claim 30, wherein the purification further comprises the steps of applying a conditioned culture medium containing the BMP-2 to a heparin-like resin, obtaining an eluate containing the BMP-2, and applying the eluate to the butyl sepharose resin.

32. A method of BMP-2 production comprising the steps of:
   i) culturing a suitable host cell comprising a DNA molecule encoding a BMP-2 protein in a culture medium comprising iron at a concentration of at least about 2.25 µM, a polyanionic compound, a total amino acid concentration of 15 mM to 40 mM, and vitamin B6 at a concentration of at least about 15 µM, and if pyridoxal is present, it makes up less than about 50% of the molar concentration of vitamin B6 in the culture medium; and
   ii) recovering a BMP-2 protein wherein the host cell is cultured in a bioreactor having a capacity greater than about 3 L.

33. The method of claim 32, wherein the culture medium further comprises copper at a concentration of at least about 10 nM.

34. The method of claim 32, wherein the culture medium further comprises zinc at a concentration of at least about 0.2 µM.

35. The method of claim 32 wherein the host cell is a CHO cell.

36. The method of claim 32, wherein the BMP-2 is rhBMP-2.

37. The method of claim 32, wherein the polyanionic compound is dextran sulfate at a concentration of at least about 10 mg/L.

38. The method of claim 32, wherein the culture medium comprises L-cystine at a concentration of at least about 0.5 mM.

39. The method of claim 38, wherein the culture medium further comprises L-glutamic acid at a concentration of at most about 0.3 mM.

40. The method of claim 32, wherein the culture medium has an initial osmolarity of between about 260 and 360 mOsm.

41. A method of BMP-2 production comprising the steps of:
   i) culturing a CHO cell comprising a DNA molecule encoding a BMP-2 protein in a batch refeed process in culture medium comprising iron at a concentration of at least about 2.25 µM, copper at a concentration of at least about 10 nM, L-cystine at a concentration of at least about 0.5 mM, dextran sulfate at a concentration of at least about 10 mg/L, a total amino acid concentration of 15 mM to 40 mM, and vitamin B6 at a concentration of at least about 15 µM, and if pyridoxal is present, it makes up less than about 50% of the molar concentration of vitamin B6 in the culture medium; and
   ii) recovering a BMP-2 protein, wherein the host cell is cultured in a bioreactor having a capacity of at least about 160 L.

42. The method of claim 41, wherein the culture medium further comprises zinc at a concentration of at least about 0.2 µM.

43. A method of BMP-2 production comprising the steps of:
   i) culturing a suitable host cell comprising a DNA molecule encoding a BMP-2 in a culture medium comprising iron at a concentration of at least about 2.25 µM, a polyanionic compound, a total amino acid concentration of 15 mM to 40 mM, and if pyridoxal is present, it is present at a concentration of less than about 15 µM; and
   ii) recovering the protein of interest wherein the host cell is cultured in a bioreactor having a capacity greater than about 3 L.

44. The method of claim 1, wherein the culture medium comprises amino acids at a total concentration of about 15 mM to 35 mM.

45. The method of claim 1, wherein the culture medium comprises amino acids at a total concentration of about 20 mM to 30 mM.

46. The method of claim 1, wherein the culture medium comprises amino acids at a total concentration of about 25 mM.

47. The method of claim 1, wherein the culture medium comprises amino acids at a total concentration of about 30 mM.

* * * * *